United States Patent
Juhászné Molnár et al.

(10) Patent No.: US 10,257,966 B2
(45) Date of Patent: Apr. 9, 2019

(54) SHIELDING DEVICE TO REDUCE THE IMPACT OF ELECTROMAGNETIC RADIATION

(71) Applicants: Marianna Juhászné Molnár, Budapest (HU); János Juhász, Budapest (HU)

(72) Inventors: Marianna Juhászné Molnár, Budapest (HU); János Juhász, Budapest (HU)

( * ) Notice: Subject to any disclaimer, the term of this patent is extended or adjusted under 35 U.S.C. 154(b) by 236 days.

(21) Appl. No.: 15/422,057

(22) Filed: Feb. 1, 2017

(65) Prior Publication Data

US 2017/0150655 A1    May 25, 2017

Related U.S. Application Data

(63) Continuation of application No. PCT/HU2015/000060, filed on Jul. 29, 2015.

(30) Foreign Application Priority Data

Aug. 1, 2014  (HU) .................................. U1400170

(51) Int. Cl.
*H05K 9/00* (2006.01)
*C12M 1/00* (2006.01)

(52) U.S. Cl.
CPC .......... *H05K 9/0007* (2013.01); *C12M 23/38* (2013.01); *C12M 45/22* (2013.01); *H05K 9/0015* (2013.01); *H05K 9/0052* (2013.01); *H05K 9/0081* (2013.01)

(58) Field of Classification Search
CPC ... H05K 9/0007; H05K 9/0052; H05K 9/0081
See application file for complete search history.

(56) References Cited

U.S. PATENT DOCUMENTS

| | | | |
|---|---|---|---|
| 7,176,387 B1 | 2/2007 | Huang | |
| 9,781,869 B2 * | 10/2017 | Molnar | H05K 9/0052 |
| 2008/0017812 A1 * | 1/2008 | Dandurand | A61N 2/06 |
| | | | 250/503.1 |
| 2008/0091238 A1 * | 4/2008 | Colliard | A61N 1/16 |
| | | | 607/3 |
| 2016/0295753 A1 * | 10/2016 | Molnar | H05K 9/0052 |
| 2016/0309627 A1 * | 10/2016 | Lehman | H04B 1/3838 |

FOREIGN PATENT DOCUMENTS

HU   226648 B1   5/2009

* cited by examiner

*Primary Examiner* — Jonathan M Hurst
(74) *Attorney, Agent, or Firm* — Molly L. Sauter; Nilay J. Choksi; Smith & Hopen, P.A.

(57) ABSTRACT

The present invention relates to a shielding device to reduce the impact of radiation, that contains a container (10) with a receptacle (14) and a functional filling (20) placed into the receptacle (14) of the container (10), where the functional filling (20) is composed of a collecting component (21) that contains a mixture of inorganic substances and a utilizing component (22) that contains a mixture of organic components.

13 Claims, 1 Drawing Sheet

SHIELDING DEVICE TO REDUCE THE IMPACT OF ELECTROMAGNETIC RADIATION

CROSS-REFERENCE TO RELATED APPLICATIONS

This application is a continuation of prior filed International Application No. PCT/HU2015/000060, filed July 29, 2015, which claims priority to Hungarian Patent Application No. U1400170, filed Aug. 1, 2014, both of which are incorporated herein by reference in their entireties.

BACKGROUND OF THE INVENTION

1. Field of the Invention

The invention relates to a shielding device to reduce the impact of electromagnetic radiation with a container that contains a receptacle and a functional filling which is placed into the receptacle of the container, where the functional filling has a collecting component composed of an inorganic mixture and a utilizing component composed of an organic mixture.

2. Brief Description of the Related Art

As a result of the current widespread use of tools of wireless information transfer such as for example mobile phones, Wi-Fi equipment, wireless short-range communication devices and cashless payment systems, electromagnetic pollution has increased considerably. Research and studies have proven that radiation overload may have an adverse impact on the comfort, life rhythm and biological and physiological processes of some living organisms such as humans among others, even resulting in health damage in extreme cases.

Several solutions have been implemented to overcome said adverse impacts. These aim at reducing or eliminating electromagnetic radiation in the area to be protected by means of conductive and shielding devices.

A solution of this kind is described for instance by the patent specification no. HU 226.648. The patent essentially describes a solution for buildings where radiation components harmful to health are mitigated by metal meshes, special paints and other shielding equipment of various structural characteristics added to the delimiting structural elements of buildings, and the electric circuit created from these conductive elements is connected to an adequate ground potential by means of discrete electric components, thus aiming at eliminating electromagnetic radiation or at least reduce it in parts of the building to be protected such as in homes.

A disadvantage of this solution, however, is the high number of structural components contained in the shielding equipment. Installing the equipment in a given building will presume major structural changes in the delimiting elements which in turn are labor intensive and as such time intensive to implement and prevent the normal use of the building for a long time.

Another disadvantage of the solution is that it is only able to shield a given person within a particular section of the building. If the person leaves this section, he/she will be still exposed to the adverse impacts of electromagnetic radiation.

Another disadvantage of the solution is that it provides protection for a limited area only, yet at very high installation costs.

The patent specification no. U.S. Pat. No. 7,176,387 also describes a shielding solution against electromagnetic radiation. Shielding is provided by a blended mesh of fibers where conductive fibers are integrated into a woven shell.

However, such a solution provides very limited protection for users, at a narrow band width only. Due to its structural design, the shielding device is vulnerable itself and tears easily when subjected to low mechanical stress, which significantly reduces its applicability and shielding capacity in particular.

BRIEF SUMMARY OF THE INVENTION

The idea for the invention was taken from known scientific observations, where compounds composed of suitable substances could divert a significant portion of electromagnetic radiation by "attracting" it and others that prove that certain living organisms are able to utilize the electromagnetic radiation they are exposed to in their metabolism and life cycles, exploiting the energy transmitted by electromagnetic radiation while eliminating its adverse impacts.

Relying on these scientific results, an idea has been developed, serving as a basis for the present invention, to create a device to collect electromagnetic radiation by designing a container of suitable shape and filling it with a suitable inorganic compound that is able to attract electromagnetic radiation and with an organic compound mixture that is able to interact with the former, as well as to use the energy flow within the electromagnetic spectrum for sustaining its life so that the container collects the electromagnetic radiation in a particular area which is then processed and utilized by living organisms specifically selected for the purpose and placed in the container, thus neutralizing a substantial part of the electromagnetic radiation in this particular area; this way local shielding against electromagnetic radiation may be easily implemented by a device of a simple structural design and thus the task of protecting an area against electromagnetic radiation may be solved.

In accordance with this goal, an aspect of the invention is a shielding device to mitigate the adverse impacts of electromagnetic radiation that comprises a container with a receptacle and a functional filling placed into the receptacle of the container, where the functional filling is composed of a collecting component made of an inorganic compound and a utilizing component made of an organic compound, designed in a way that the utilizing component of the functional filling includes a compound with microorganisms that contains lactic acid bacteria in 23 to 27% (v/v) and yeast in 23 to 27% (v/v) dispersed in potassium silicate (16 to 20% (v/v)) and/or graphite (8 to 12% (v/v)) and/or in a gold and bronze powder (20 to 24% (v/v)), while the collecting component of the functional filling is a compound composed of cobalt (10 to 14% (v/v)) and/or iron (14 to 18% (v/v)) and/or molybdenum (10 to 14% v/v)) and/or niobium (13 to 17% (v/v)) and/or silicon (12 to 16% (v/v)) and/or boron (13 to 17% (v/v)) and/or silver (14 to 18% (v/v)), and the container has a housing in the form of a solid superficies which with a filler hole and the filler hole of the housing is covered by a lid.

In another aspect of the invention there is provided a gas-proof sealing at the connection of the housing of the container and its lid.

In another design of the invention there is provided a porous bearing component which is impregnated with the utilizing component of the functional filling and thus by means of the bearing component the utilizing component of the functional filling is placed into the receptacle of the container.

In another design of the invention there is provided a collecting component of the functional filling and it is applied (e.g. by thermal evaporation) on the plastic carrier component in a thickness of 10 to 30 micron and thus placed in the receptacle of the container by means of the carrier component. Where appropriate, the carrier component is placed onto the inner side of the lid of the container.

In another aspect of the present invention the outer side of the lid of the container is treated with a fixing component e.g. a layer of glue.

In another form of the invention there is provided a housing and/or a lid made of plastic, e.g. of synthetic resin, or a housing and/or a lid made of metal, e.g. of stainless steel.

The innovation has several beneficial features. The most important one of these is that the shielding device is able to efficiently shield relatively large areas against electromagnetic radiation while having a limited space demand only due to its unique container and the filling of a unique composition placed into it.

Another advantage of the solution is that both the container and the filling are simple to manufacture and the filling may be safely placed into the housing by simple means.

Yet another advantage of the solution is that its use does not require any specific expertise. The structural design of the housing, the way it is closed and the composition of the filling minimize the chance of malfunction thus the service life of the device is rather long. It does not require maintenance or any kind of intervention once installed.

Yet another advantage of the solution is that its simple structure and operation facilitates seamless and prompt relocation, without any specific expertise or skills, promoting a broad applicability.

Accordingly, yet another advantage of the solution is that its low space demand and simple operation facilitates broad penetration which in turn may significantly reduce the adverse health effects of electromagnetic radiation, resulting in beneficial externalities at the level of the society in general due to diminishing medical costs.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
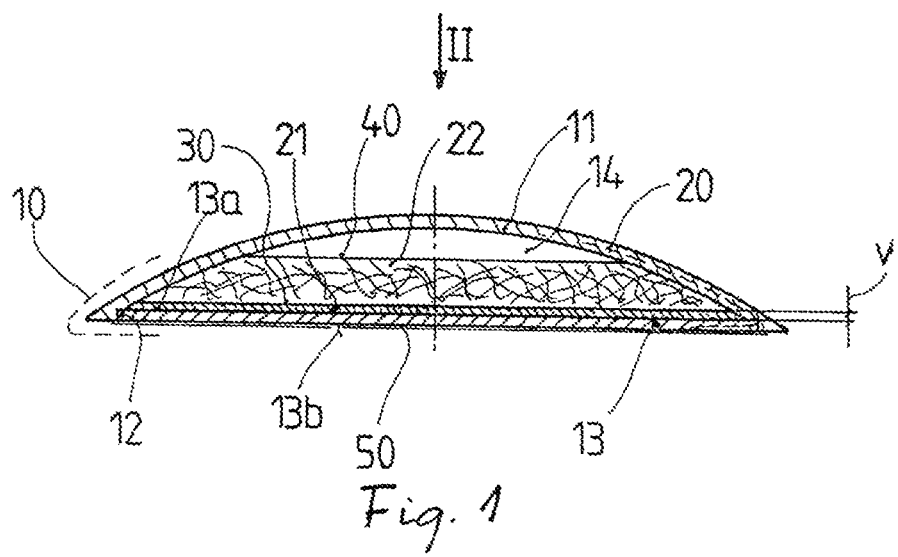
FIG. 1 shows a particular embodiment of the invention from side view, partly in a cutaway view.

The characteristic feature of the invention is that, the utilizing component (22) of the functional filling (20) includes a compound with microorganisms that contains lactic acid bacteria in 23 to 27% (v/v) and yeast in 23 to 27% (v/v) dispersed in potassium silicate 16 to 20% (v/v) and/or graphite 8 to 12% (v/v) and/or in a gold and bronze powder 20 to 24% (v/v), while the collecting component (21) of the functional filling (20) is a compound composed of cobalt 10 to 14% (v/v) and/or iron 14 to 18% (v/v) and/or molybdenum 10 to 14% v/v) and/or niobium 13 to 17% (v/v) and/or silicon 12 to 16% (v/v) and/or boron 13 to 17% (v/v) and/or silver 14 to 18% (v/v), and the container (10) has a housing (11) in the form of a solid superficies with a filler hole (12) and the filler hole (12) of the housing (11) is covered by a lid (13).

Figure 2:
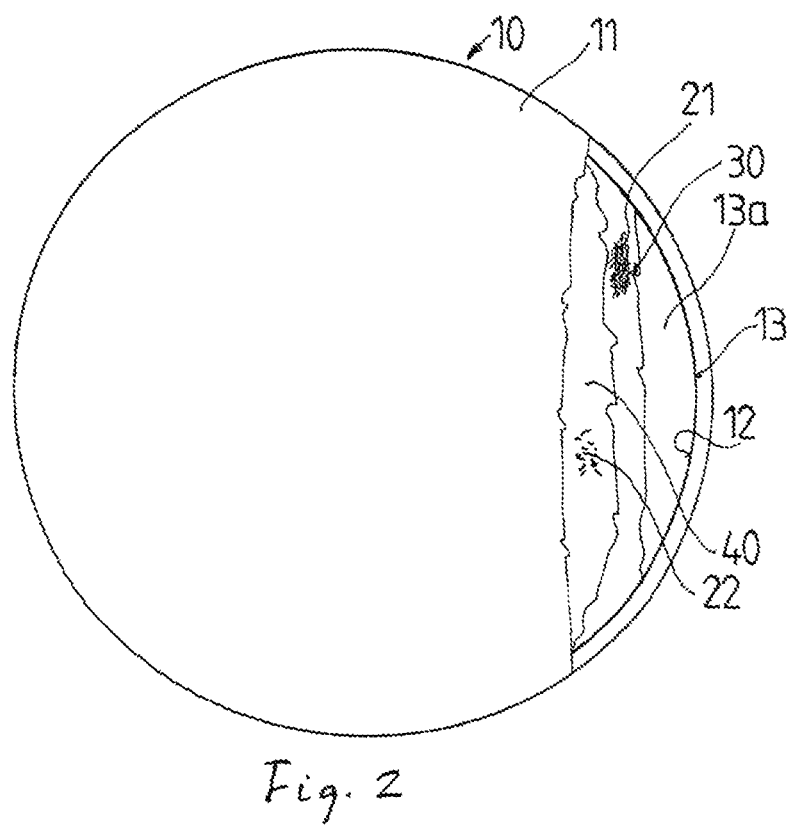
FIG. 2 shows the shielding device of FIG. 1 from View II.

FIG. 1 and FIG. 2 show a particular embodiment of the invention that is suitable for eliminating the radiation emitted by mobile phones as sources of electromagnetic radiation, thus reducing the local radiation load on the user.

We should note here that depending on its size the shielding device is not only able to trap the radiation emitted by a given mobile phone but also the ambient electromagnetic radiation in the vicinity of the device, thus reducing the general radiation load in the direct vicinity of the user.

As illustrated by the drawing, the external design of the 10 container of the shielding device in this particular embodiment forms a spherical section, defined by the 11 housing and the 13 lid. In this particular embodiment, the 11 housing and the 13 lid are made of metal, e.g. stainless steel. We should note here, however, that the 11 housing of the 10 container and/or its 13 lid may also be made of other substances, e.g. of sufficiently strong plastic.

The combination of the 11 housing and the 13 lid encloses the 14 receptacle whose 12 filler hole is closed by the 13 lid. To facilitate proper operation, once the 20 functional filling is placed inside, the connection of the 11 housing and the 13 lid is sealed in a gas-proof way. The 20 functional filling includes the 21 collecting component and the 22 utilizing component.

The 21 collecting component of the 22 functional filling is a compound composed of cobalt (10 to 14% (v/v)) and/or iron (14 to 18% (v/v)) and/or molybdenum (10 to 14% v/v)) and/or niobium (13 to 17% (v/v)) and/or silicon (12 to 16% (v/v)) and/or boron (13 to 17% (v/v)) and/or silver (14 to 18% (v/v)), which in this particular embodiment of the invention contains cobalt powder (12% (v/v)), iron powder (16% (v/v)), molybdenum powder (12% (v/v), niobium powder (14% (v/v)), silicon powder (14% (v/v)), boron (15% (v/v)) and silver powder (16% (v/v) applied by e.g. thermal evaporation or by brush on the 30 carrier component placed on the 13a inner side of the 13 lid of the 14 receptacle of the 10 container. The 30 carrier component may be a suitably thin plastic sheet of preferably 10 to 30 micron in "v" thickness that does not enter into a reaction with the inorganic substances in the 21 collecting component.

The 22 utilizing component of the 20 functional filling includes a compound with microorganisms that contains lactic acid bacteria in 23 to 27% (v/v) and yeast in 23 to 27% (v/v) dispersed in potassium silicate (16 to 20% (v/v)) and/or graphite (8 to 12% (v/v)) and/or in a gold and bronze powder (20 to 24% (v/v)). In this particular embodiment of the invention, the 22 functional component contains lactic acid bacteria (25% (v/v)) and yeast (25% (v/v)) dispersed in potassium silicate (18% (v/v)), graphite (10% (v/v)) and a gold and bronze powder (22% (v/v)) as a utilizing component, and there is provided a porous 40 bearing component which is impregnated with this composition thus by means of the 40 bearing component the composition is placed into the 14 receptacle of the 10 container.

To install the invention to its intended place and fix it there, in this particular embodiment of the invention there is provided a 50 fixing component on the 13b outer side of the 13 lid of the 10 container. In this particular case, the 50 fixing component is a layer of glue that serves the purpose of fixing the shielding device on e.g. the case of a mobile phone.

The invention is manufactured as follows. First, the 11 housing of the 10 container, in the form of a solid superficies, and the 13 lid that can close the 12 filler hole of the 14 receptacle should be manufactured by a known process such as e.g. deep drawing, chipping or molding in the case of metals or e.g. injection molding or injection compression molding in the case of plastics.

Furthermore, the mixture of the 21 collecting component of the 20 functional filling should be composed and then applied e.g. by thermal evaporation on the surface of the 30 carrier component. The substances of the 22 utilizing component of the 20 functional filling should also be measured out and the 40 bearing component should be impregnated with the mixture.

Following these preparatory steps, first the 40 bearing component impregnated with the 22 utilizing component should be placed into the 14 receptacle of the 11 housing of the 10 container, then the 30 carrier component treated with the 21 collecting component of the 20 functional filling should be placed on top of it. Finally, the 12 filler hole of the 11 housing can be closed with the 13 lid in a known way to provide for gas-proof sealing.

Once all these steps have been completed, the shielding device is ready for use. To install the shielding device at its intended place and fix it there, a 50 fixing component is provided on the 13b outer side of the 13 lid which is, in the case of e.g. a layer of glue, serves the purpose of fixing the 10 container on a given surface in a given position, like e.g. on the back panel of a mobile phone.

During use, the 21 collecting component in the 14 receptacle of the 10 container collects a significant portion of the ambient electromagnetic radiation. As the 21 collecting component is located directly by the 22 utilizing component, the energy transmitted by the electromagnetic radiation of a particular wave length collected by the 21 collecting component will accumulate near the microorganisms of the 22 utilizing component and will be utilized by these microorganisms for sustaining their lives, thus the electromagnetic radiation in the vicinity of the shielding device will be significantly reduced or eliminated.

Obviously, the dimensions and (when justified) the design of the 11 housing of the 10 container of the shielding device is optimized for particular tasks; however, the spherical section design is suitable in most of the cases.

The invention represents a good solution in all the cases where the magnitude and the impact of the electromagnetic radiation loading the environment should be diminished or the radiation eliminated.

LIST OF REFERENCES 10 container
11 housing
12 filler hole
13 lid
13a inner side
13b outer side
14 receptacle
20 functional filling
21 collecting component
22 utilizing component
30 carrier component
40 bearing component
50 fixing component
"v" thickness

What is claimed is:

1. A shielding device to reduce the impact of radiation, comprising:
a container with a receptacle; and
a functional filling positioned in the receptacle of the container, where the functional filling is composed of a collecting component that contains a mixture of inorganic substances and a utilizing component that contains a mixture of organic components,
wherein the utilizing component of the functional filling includes a compound with microorganisms that contain lactic acid bacteria in 23% to 27% (v/v) and yeast in 23% to 27% (v/v) dispersed in potassium silicate 16% to 20% (v/v) and/or graphite 8% to 12% (v/v) and/or in a gold and bronze powder 20% to 24% (v/v),
wherein the collecting component of the functional filling is a compound composed of cobalt 10% to 14% (v/v) and/or iron 14% to 18% (v/v) and/or molybdenum 10% to 14% (v/v) and/or niobium 13% to 17% (v/v) and/or silicon 12% to 16% (v/v) and/or boron 13% to 17% (v/v) and/or silver 14% to 18% (v/v),
wherein the container has a housing in the form of a solid superficies with a filler hole, where the filler hole of the housing is covered by a lid.

2. A shielding device as in claim 1, wherein a sealing at the connection of the housing of the container and its lid is gas-proof.

3. A shielding device as in claim 1, further comprising a porous bearing component impregnated with the utilizing component of the functional filling, wherein the porous bearing component permits the utilizing component of the functional filling to be positioned in the receptacle of the container.

4. A shielding device as in claim 1, wherein the collecting component of the functional filling is applied on a plastic carrier component in a thickness of 10 to 30 micron and thus positioned in the receptacle of the container by means of the carrier component.

5. A shielding device as in claim 4, wherein the collecting component of the functional filling is applied on the plastic carrier via thermal evaporation.

6. A shielding device as in claim 4, wherein the carrier component is positioned on an inner side of the lid of the container.

7. A shielding device as in claim 1, wherein an outer side of the lid of the container is treated with a fixing component.

8. A shielding device as in claim 7, wherein the fixing component is a layer of glue.

9. A shielding device as in claim 1, wherein the housing and/or the lid is formed of a plastic.

10. A shielding device as in claim 9, wherein the plastic is synthetic resin.

11. A shielding device as in claim 1, wherein the housing and/or the lid is formed of a metal.

12. A shielding device as in claim 11, wherein the metal is stainless steel.

13. A shielding device to reduce the impact of electromagnetic radiation, comprising:
a container with a receptacle;
a functional filling positioned in the receptacle of the container, where the functional filling is composed of a collecting component that contains a mixture of inorganic substances and a utilizing component that contains a mixture of organic components,
wherein the utilizing component of the functional filling includes a compound with microorganisms that contain lactic acid bacteria in 23% to 27% (v/v) and yeast in 23% to 27% (v/v) dispersed in potassium silicate 16% to 20% (v/v) and graphite 8% to 12% (v/v) and in a gold and bronze powder 20% to 24% (v/v), wherein the collecting component of the functional filling is a compound composed of cobalt 10% to 14% (v/v) and iron 14% to 18% (v/v) and molybdenum 10% to 14% (v/v) and niobium 13% to 17% (v/v) and silicon 12% to 16% (v/v) and boron 13% to 17% (v/v) and silver 14% to 18% (v/v), wherein the container has a housing in the form of a solid superficies with a filler hole, where the filler hole of the housing is covered by a lid, wherein a sealing at the connection of the housing of the container and its lid is gas-proof, wherein an outer side of the lid of the container is treated with a layer of glue; and a porous bearing component impregnated with the utilizing component of the functional filling, wherein the porous bearing component permits the utilizing component of the functional filling to be positioned in the receptacle of the container, wherein the collecting component of the functional filling is applied on a plastic carrier component via thermal evaporation in a thickness of 10 to 30 micron and thus positioned in the receptacle of the container by means of the carrier component, wherein the carrier component is positioned on an inner side of the lid of the container.

\* \* \* \* \*